(12) United States Patent
Koch et al.

(10) Patent No.: US 6,858,726 B2
(45) Date of Patent: Feb. 22, 2005

(54) SYNTHESIS OF ALLOFURANOSE

(75) Inventors: Troels Koch, Copenhagen (DK); Henrik Frydenlund Hansen, Rødovre (DK)

(73) Assignee: Santaris Pharma A/S, Horsholm (DK)

( * ) Notice: Subject to any disclaimer, the term of this patent is extended or adjusted under 35 U.S.C. 154(b) by 0 days.

(21) Appl. No.: 10/165,768

(22) Filed: Jun. 7, 2002

(65) Prior Publication Data

US 2003/0023080 A1 Jan. 30, 2003

Related U.S. Application Data

(60) Provisional application No. 60/296,625, filed on Jun. 7, 2001.

(51) Int. Cl.[7] .................................................. C07H 1/00
(52) U.S. Cl. ......................................................... 536/124
(58) Field of Search ................................ 536/124, 1.11

(56) References Cited

FOREIGN PATENT DOCUMENTS

| EP | 0 379 397 | 7/1990 |
|---|---|---|
| WO | WO 00 56748 | 12/2000 |

OTHER PUBLICATIONS

David C. Baker et al, Carbohydrate Research, 1972, 24, 192–197.*

Sowa, W. et al "The Oxidation of 1,2:5,6–Di–O–Isopropylidene–D–Glucose By Dimethyl Sulfoxide–Acetic Anhydride", Canadian Journal of Chemistry, 1966, 44, 836–838.*

Fuertes, C. M., *Boletin De La Sociedad Quimica Del Peru*, vol. 37, No. 4, 1971, pp. 161–174 [English translation].

Singh, S.K., et al., J.Chem. Commun, pp. 455–456, 1998.

Koshkin, A.A., et al., Tetrahedron, pp. 3607–3630, 1998.

Albright, A.D., e al., Journal of the American Chemical Society, pp. 2416–2423.

Horton, D., et al., Carbohydrate Res. pp. 251–260, 1966.

Horton, D., et al., Carbohydrate Res. pp. 229–232, 1968.

Baker, D.C., et al., Carbohydrate Res. pp. 192–197, 1972.

Sowa, W., et al., Canadian J. Org. Chem. pp. 836–838, 1966.

Youssefyeh, R.D., et al., J. Org. Chem. pp. 1301–1309, 1979.

\* cited by examiner

*Primary Examiner*—James O. Wilson
*Assistant Examiner*—Ganapathy Krishnan
(74) *Attorney, Agent, or Firm*—Peter F. Corless; Christine C. O'Day; Edwards & Angell, LLP

(57) ABSTRACT

The present invention provides a novel strategy for the synthesis of allofuranose using glucofuranose as starting material in a one-pot reaction. The novel finding is that it is possible to carry out the oxidation of 1,2:5,6-di-O-isopropylidene-α-D-glucofuranose with DMSO/acetic anhydride and a reduction reaction in one pot obtaining high yields of recrystallised and analytical pure 1,2:5,6-di-O-isopropylidene-α-D-allofuranose.

16 Claims, No Drawings

US 6,858,726 B2

SYNTHESIS OF ALLOFURANOSE

The present application claims the benefit of U.S. provisional application No. 60/296,625 filed Jun. 7, 2001, which is incorporated by reference herein in its entirety.

FIELD OF THE INVENTION

The present invention relates to a new strategy for the synthesis of α-D-allofuranose, which is to be used for large-scale production of LNA (Locked Nucleic Acid) analogues with higher overall yields, and more cost efficient than previously known methods.

BACKGROUND OF THE INVENTION

Synthesis of LNA (Locked Nucleic Acid) monomers were first reported by Wengel et al (Singh, S. K.; Nielsen, P., Koshkin, A. A. and Wengel, *J. Chem. Commun.*, 1998, 455; Koshkin, A. A.; Singh, S. K.; Nielsen, P.; Rajwanshi, V. K.; Kumar, R.; Melgaard, M; Olsen, C. E. and Wengel, J., *Tetrahedron*, 1998, 54, 3607). Depending on which monomer that is prepared, LNA monomer synthesis consists of 15–17 steps. Due to the length of the synthesis it is very important that all steps proceed in the most optimal way. The synthesis steps are optimised on four parameters:

1. Fast reaction time
2. Employing cheap reagents
3. Easy to handle
4. Proceeds in high overall yields In the procedures cited in the art the starting material was 1,2:5,6-di-O-isopropylidene-α-D-allofuranose. 1,2:5,6-di-O-isopropylidene-α-D-allofuranose is commercially available (e.g. at Pfanstiel, CAS Number: 2595-05-03). Reducing the cost of the starting material by improving the synthesis is of great value for LNA synthesis.

1,2:5,6-di-O-isopropylidene-α-D-allofuranose is normally prepared from the much cheaper 1,2:5,6-di-O-isopropylidene-α-D-glucofuranose in two steps. The first step is oxidation of the secondary alcohol which is subsequently reduced to provide the allo-configuration. Oxidation of secondary hydroxyl groups to their corresponding carbonyl derivatives with dimethyl sulfoxide (DMSO) and acetic anhydride has been described (Albright J. D. and Goldman L., *J. Am. Chem. Soc.*, 1967, 89:10). The oxidation of alcohols with acetic anhydride-DMSO is described to be a mild oxidative method and giving good yields with sterically hindered hydroxyl groups. They demonstrate in the paper that optimal oxidation is found in the case when ca. 20 times excess of acetic anhydride in relation to the alcohol, is used. All the experiments are performed on alkaloids and on steroids, thus no examples on furanoses are shown.

Also Horton D. and Jewell J. S. (*Carbohydrate Res.*, 1966, 2, 251–260) and Horton, D. and Godman, J. L. (*Carbohydrate Res.*, 1968, 6, 229–232) have used DMSO/Acetic anhydride but they point out that it is important to remove the reagents (DMSO/acetic anhydride) before further reactions and they use either evaporation at reduced pressure or lyophilation to remove the reagents. To carry out the reaction they use an excess of acetic anhydride between 7 and 26 fold.

Baker D. C. et al. (Baker D. C., Horton D. and Tindall C. G., *Carbohyd. Res.*, 1972, 24 192–197) show that acetic anhydride/DMSO oxidation can be applied to 1,2:5,6-di-O-isopropylidene-α-D-glucofuranose and they underline that the method is not effective on large scale. For their large scale synthesis, 0.5 mole 1,2:5,6-di-O-isopropylidene-α-D-glucofuranose, they use a complex reaction mixture composed of chloroform, water, potassium metaperiodate, potassium carbonate, and the rare earth metal ruthenium dioxide. After a rather laborious work-up the hydrated ketone is isolated. Thus, they illustrate in this paper that it is not possible to mix the subsequent reduction step with the oxidation step. The overall yield of these two consecutive steps is 64% of crude material. Furthermore, they claim that the DMSO/Acetic anhydride oxidation is not suitable for larger batches>0.5 mole.

Sowa, W. and Thomas, G. H. S., (*Can. J. of Chem.*, 1966, Vol. 44, 836–838) used the DMSO/acetic anhydride oxidation of 1,2:5,6-di-O-isopropylidene-α-D-glucofuranose in small scale (10 mmole) using a 20 fold excess of acetic anhydride. The ulose was then reduced providing 1,2:5,6-di-O-isopropylidene-α-D-allofuranose of poor quality, thus the product had to be column purified. Overall this procedure is not suitable for large-scale productions due to the large reagent consumption, two step procedure and the column purification step.

Youssefyeh R. D. et al. (Youssefyeh, R. D., Verhyden, J. P. H., Moffatt, J. G., *J. Org. Chem.* 1979, 44(8), 1301–1309) employed the DMSO/Acetic anhydride oxidation and subsequent the reduction with sodium borohydride to prepare 1,2-O-isopropylidene-5-O-trityl-4-(trityloxymethyl)-α-D-erythro-pentofuranose from the corresponding threo derivative. Like Baker D. C. et al. they used a large excess of acetic anhydride (10 times) and performed the reaction in small scale (2.13 mmole).

Fuertes C. M. and Cesar M. (*Bol. Soc. quim. Peru*, 1972. 37(4), 161–74,) prepared 1,2:5,6-di-O-isopropylidene-α-D-allofuranose by a consecutive two step reaction from 1,2:5, 6-di-O-isopropylidene-α-D-glucofuranose. However, they used a 13 fold excess of acetic anhydride and allowed the oxidation to proceed for 72 h. The yield in the oxidation step was 60%. The subsequent reduction was performed in 75% yield, thus the overall yield in the sequential reactions was 45%.

SUMMARY OF THE INVENTION

The present invention provides a novel strategy for the synthesis of allofuranose using glucofuranose as starting material in a one-pot reaction. The novel finding is that it is possible to carry out the oxidation of 1,2:5,6-di-O-isopropylidene-α-D-glucofuranose with DMSO/acetic anhydride and a reduction reaction in one pot obtaining high yield of recrystallised and analytically pure 1,2:5,6-di-O-isopropylidene-α-D-allofuranose.

The main advantages of the present invention comprise the following:

One-pot reaction

Better yield than previously reported two-step reactions

Lower reagent consumption

Easy work-up

Ready to scale up

All the impurities are removed in a simple extraction step without using chromatography. Chromatography is not suitable for large-scale synthesis.

DETAILED DESCRIPTION OF THE INVENTION

The surprising finding according the present invention is that it is possible to carry out the oxidation of 1,2:5,6-di-O-isopropylidene-α-D-glucofuranose with DMSO/acetic anhydride in one pot with the subsequent reduction of the 1,2:5,6-di-O-isopropylidene-α-D-ribofuranose-3-ulose to form 1,2:5,6-di-O-isopropylidene-α-D-allofuranose (formula I). It is very surprising that the reduction can be carried out in the presence of the oxidation mixture. It is also surprising that it is possible to use this oxidation procedure in large scale (1 mole), and that the lowest reported amount of excess acetic anhydride (5 times) provides 58 % yield of recrystallised and analytical pure 1,2:5,6-di-O-isopropylidene-α-D-allofuranose.

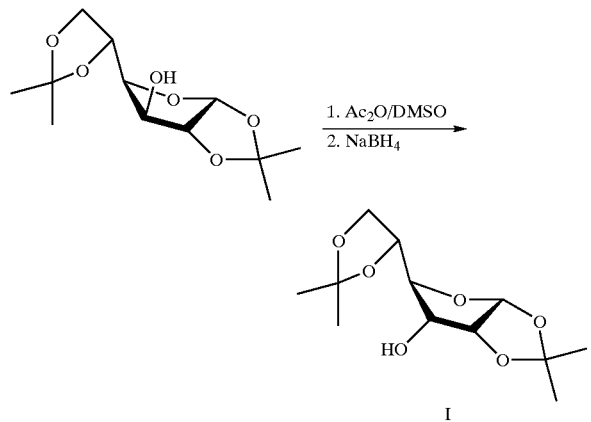

I

Thus, the combination of a facile one-pot reaction employing a minimum of reagent consumption makes the synthesis 1,2:5,6-di-O-isopropylidene-α-D-allofuranose much more cost effective. Also noteworthy is the fact that the work-up is very easy and that no column purification is needed to provide an analytical pure and crystalline product.

Although the invention has been developed based on the isopropylidene-protected sugars, it is believed that other protection groups of the acetal type may be applicable. Thus, the protective group used according to the present is typically an acetal such as isopropylidene, cyclohexylidene or benzylidene. 1,2:5,6-di-O-isopropylidene-α-D-glucofuranose is commercially available and other protected glucofuranose derivatives are easily obtainable from glucose and the appropriate aldehyde/ketone using acid catalysis. The oxo compounds (aldehyde/ketone) may be used directly but may also be used as the corresponding alkylacetals/ketals. The acid catalysis may be effected by proton or Lewis acids as known in the art.

The oxidation reaction according to the present invention is preferably carried out using DMSO and an acid anhydride as an oxidising system. A preferred anhydride is acetic anhydride. The preferred molar ratio between 1,2:5,6-di-O-isopropylidene-α-D-glucofuranose and acetic anhydride is in the range of 1:3 and 1:9 and more preferably between 1:5 and 1:7. Other oxidising reagents such as N-halo-succinimides, chlorine, hypohalites, potassium metaperiodate-ruthenium dioxide, DMSO-N,N'-dicyclohexylcarbodiimide-pyridinium phosphate, DMSO-phosphorous pentaoxide, and chromium trioxide-pyridine complex may also be used.

In the present invention DMSO can be used as reagent and solvent but DMSO may also be used in combinations with other solvents so that the concentration of DMSO is reduced. Such solvents may not interfere with the oxidation/reduction reaction and would typically be polar non-protic solvents like NMP and DMF.

The oxidising reaction is typically be carried out at ambient temperature but the reaction can also be carried out at elevated temperatures. Typically temperatures in the range from 18–100° C. preferable in the range from 20–70° C. The reaction will typically take from 1–48 h but the reaction time will preferably be in the range from 10–25 h.

The reduction reaction according to the present invention is typically performed using a reducing agent, typically a metal complex, that gives a high stereospecific yield of the allofuranose. Illustrative example of reducing agents are borohydrides for example sodium borohydride; borane; and aluminium hydrides such as lithium aluminium hydride and sodium bis (2-methoxyethoxy)aluminium hydride ("Vitride").

The reduction reaction is typically carried out at ambient temperature but the reaction can also be carried out elevated temperatures. Typically temperatures in the range from 18–70° C. preferable in the range from 20–40° C. The reaction will typically take from 0.5–5 h but the reaction time will preferably be in the range from 1–3 h.

The yield of allofuranose obtained from the reaction according to the present invention, using glucofuranose as starting material, is in the range of 40%–90%, typically in the range of 50–70%.

In a preferred embodiment of the method according to the invention, 1,2:5,6-di-O-isopropylidene-α-D-glucofuranose is reacted with a mixture of DMSO and acetic anhydride in a molar ratio of 1:3 to 1:9 at 20–25° C., for around 12–48 h, typically for around 24 h, followed by reaction with sodium borohydride at 20–25° C., for around 0.5–2 h, typically for around 1 h, in order to yield 1,2:5,6-di-O-isopropylidene-α-D-allofuranose. The two reactions are performed sequentially, i.e. without isolation or purification of the intermediate product, i.e. the ulose.

In one embodiment of the present invention the allofuranose is subsequently used in the synthesis of an LNA monomer, i.e. a conformationally locked nucleoside, e.g. as described in WO 99/14226 and subsequent WO 00/56746, WO 00/56748, WO 00/66604.

Thus, the method of the invention is particularly applicable for the production of an LNA monomer.

The invention has been described with reference to preferred embodiments thereof. However, it will be appreciated that those skilled in the art, upon consideration of this disclosure, may make modifications and improvements within the spirit and scope of the invention. The following non-limiting examples are illustrative of the invention.

EXAMPLES

Synthesis of 1,2:5,6-di-O-isopropylidene-α-D-allofuranose 1,2:5,6-di-O-isopropylidene-α-D-glucofuranose 260 g (1 mole) was stirred for 24 h in DMSO 2000 ml and Ac$_2$O 500 ml (5 mole) at RT. By that time, TLC (DCM (dichloromethane)/MeOH 95:5) indicated complete reaction of the starting material. The solution was then cooled to 0° C. and sodium borohydride 16 g (0.42 mole) was added portion wise. By that time, TLC (DCM/MeOH 95:5) indicated complete formation of the target compound, approx. 1 h, water 2500 ml was added and the solution was extracted with DCM 3×1000 mL. The combined organic phases was washed with water 2×1000 ml and brine and dried with magnesium sulfate and evaporated to an oil. To the oil was added tert-butyl methylether (300 mL) and extracted with water 2×750 mL. The combined water phases were extracted with dichloroethane 2×400 mL. The combined organic phases was dried with magnesium sulfate and evaporated to an oil. Crystallisations twice from cyclohexane, 500 ml and 300 ml respectively, gave 151 g (58%) of pure 1,2:5,6-di-O-isopropylidene-α-D-allofuranose.

NMR (CDCl$_3$): 1.30 (s, 3, CH3), 1.32 (s, 3, CH3), 1.40 (s, 3, CH3), 1.51 (s, 3, CH3), 2.45 (d, 1, OH), 3.75 (q, 1, H-6), 4.00 (m, 3, H-4, H-5, H-7), 4.23 (m, 1, H-3), 4.55 (q, 1, H-2), 5.74 (m, 1, H-1).

TLC spray: Ketone—100 mg DNPH, 90 mL EtOH, 10 ml konc. HCl Ketone and or product—2 M H$_2$SO$_4$.

We claim:

1. A method for the synthesis of allofuranose or a protected form thereof wherein the starting material is glucofuranose comprising a protecting group, the reaction is a one-pot reaction comprising an oxidation reaction and a reduction reaction and wherein the reduction reaction is carried out in the presence of the oxidation mixture.

2. A method according to claim 1, wherein the protecting group is an acetal protective group.

3. A method according to claim 1, wherein the glucofuranose is 1,2:5,6 protected.

4. A method according to claim 3, wherein the glucofuranose is 1,2:5,6-di-O-isopropylidene-α-D-glucofuranose.

5. A method according to claim 3, wherein the 1,2 and 5,6 protecting groups are acetal groups.

6. A method according to claim 5 wherein the acetal groups are independently selected from the group consisting of isopropylidene, cyclohexylidene and benzylidene.

7. A method according to claim 1, wherein the allofuranose is 1,2:5,6-di-isopropylidene-α-D-allofuranose.

8. A method according to claim 1, wherein the oxidation is performed using DMSO and acid anhydride as an oxidizing system.

9. A method according to claim 8, wherein the acid anhydride is acetic anhydride.

10. A method according to claim 1, wherein the oxidation is performed using DMSO-phosphorous pentaoxide as an oxidizing system.

11. A method according to claim 1 wherein the oxidation comprises use of an an oxidation system selected from the group consisting of N-halo-succinimides, chlorine, hypohalites, potassium metaperiodate-ruthenium dioxide, DMSO and acetic anhydride in a molar ratio of 1:3 to 1:9, DMSO-N,N'-dicyclohexylcarbodiimide-pyridinium phosphate, DMSO-phosphorous pentaoxide, and chromium trioxide-pyridine complex.

12. A method according to claim 1, wherein the reduction is performed using a metal hydride complex.

13. A method according to claim 1, wherein the reduction is performed using a reducing agent selected from the group consisting of borohydride, boran, and aluminium hydride.

14. A method according to claim 13, wherein the borohydride is sodium borohydride.

15. A method according to claim 13, wherein the aluminium hydride is selected from lithium aluminium hydride and sodium bis(2-methoxyethoxy)aluminium hydride.

16. A method according to claim 1 further comprising crystallization of allofuranose or a protected form thereof.

* * * * *